United States Patent
West

(10) Patent No.: US 6,689,075 B2
(45) Date of Patent: Feb. 10, 2004

(54) POWERED GAIT ORTHOSIS AND METHOD OF UTILIZING SAME

(75) Inventor: R. Gary West, Birmingham, AL (US)

(73) Assignee: HealthSouth Corporation, Birmingham, AL (US)

( * ) Notice: Subject to any disclaimer, the term of this patent is extended or adjusted under 35 U.S.C. 154(b) by 338 days.

(21) Appl. No.: 09/938,825

(22) Filed: Aug. 27, 2001

(65) Prior Publication Data

US 2002/0026130 A1 Feb. 28, 2002

Related U.S. Application Data

(60) Provisional application No. 60/227,597, filed on Aug. 25, 2000.

(51) Int. Cl.[7] ............................. A61H 1/00; A61H 3/04; A61F 5/00
(52) U.S. Cl. ............................... 601/23; 602/23; 482/69
(58) Field of Search ............................ 482/54, 69, 66; 601/23, 33, 35; 434/255, 307 R; 602/36, 23; 607/49

(56) References Cited

U.S. PATENT DOCUMENTS

| | | |
|---|---|---|
| 4,907,571 A | 3/1990 | Futakami |
| 4,973,044 A | 11/1990 | Jones |
| 5,020,790 A | 6/1991 | Beard et al. |
| 5,190,507 A | 3/1993 | Iijima |
| 5,273,502 A | 12/1993 | Kelsey et al. |
| 5,466,213 A | 11/1995 | Hogan et al. |
| 5,476,441 A | * 12/1995 | Durfee et al. ............ 602/23 |
| 5,502,851 A | 4/1996 | Costello |
| 5,569,129 A | 10/1996 | Seif-Naraghi et al. |
| 5,662,560 A | 9/1997 | Svendsen et al. |
| 5,667,461 A | 9/1997 | Hall |
| 5,695,432 A | 12/1997 | Soderlund |
| 5,795,269 A | 8/1998 | Bawtree et al. |
| 5,865,770 A | 2/1999 | Schectman |
| 5,961,541 A | 10/1999 | Ferrati |
| 5,997,444 A | 12/1999 | McBride |

OTHER PUBLICATIONS

G. Sinha, "Disabled Rehab Takes Big Step" in Popular Science, Apr. 2001, p. 39.
G. Colombo et al., "Treadmill Training of Paraplegic Patients Using a Robotic Orthosis" in J. of Rehabilitation R&D, vol. 37, No. 6, Nov./Dec. 2000.

* cited by examiner

Primary Examiner—Stephen R. Crow
(74) Attorney, Agent, or Firm—Dykema Gossett PLLC

(57) ABSTRACT

A support structure supports powered lifting means for lifting a patient from a wheelchair and moving the patient over a powered treadmill where the patient is lowered onto the treadmill. A control panel with a mirror thereon is supported at one end of the support structure, and a touch screen data entry/display device is supported by the panel. Two similar housings are disposed at opposite sides of the treadmill. Each housing pivotally supports a support arm which can swing away from the treadmill to facilitate access to the treadmill. Each support arm pivotally supports a first depending arm, and a second depending arm is pivotally supported therefrom. A pair of servo motors are supported by each support arm and are drivingly connected to the first and second depending arms to independently move the depending arms about the pivot axes thereof. A first attachment cuff is connected to the first depending arm for attachment to a patient's leg just above the knee. A second attachment cuff is connected to the second depending arm for attachment to a patient's ankle. The support arms are vertically adjustable, and the attachment cuffs are horizontally adjustable. The first attachment cuff is vertically adjustable, and the second attachment cuff floats vertically relative to its depending arm. Control means is connected to the drive means for the treadmill and the servo motors which move the depending arms to cause the treadmill and the depending arms to operate in a coordinated manner to cause the legs of the patient to move in a desired gait. Sensor means is also provided for sensing the home position as well as possible over-travel of the knee joint of the device.

30 Claims, 16 Drawing Sheets

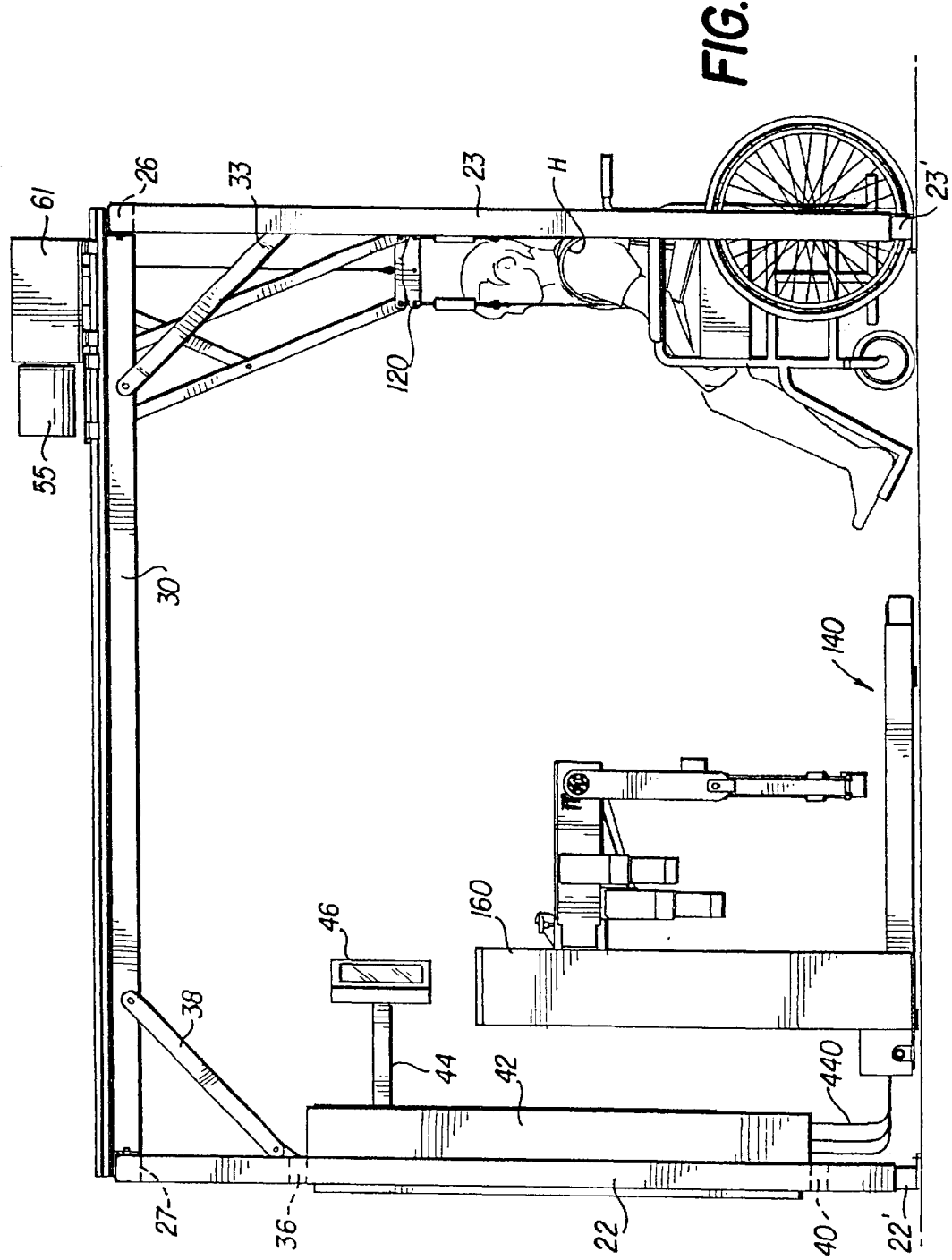

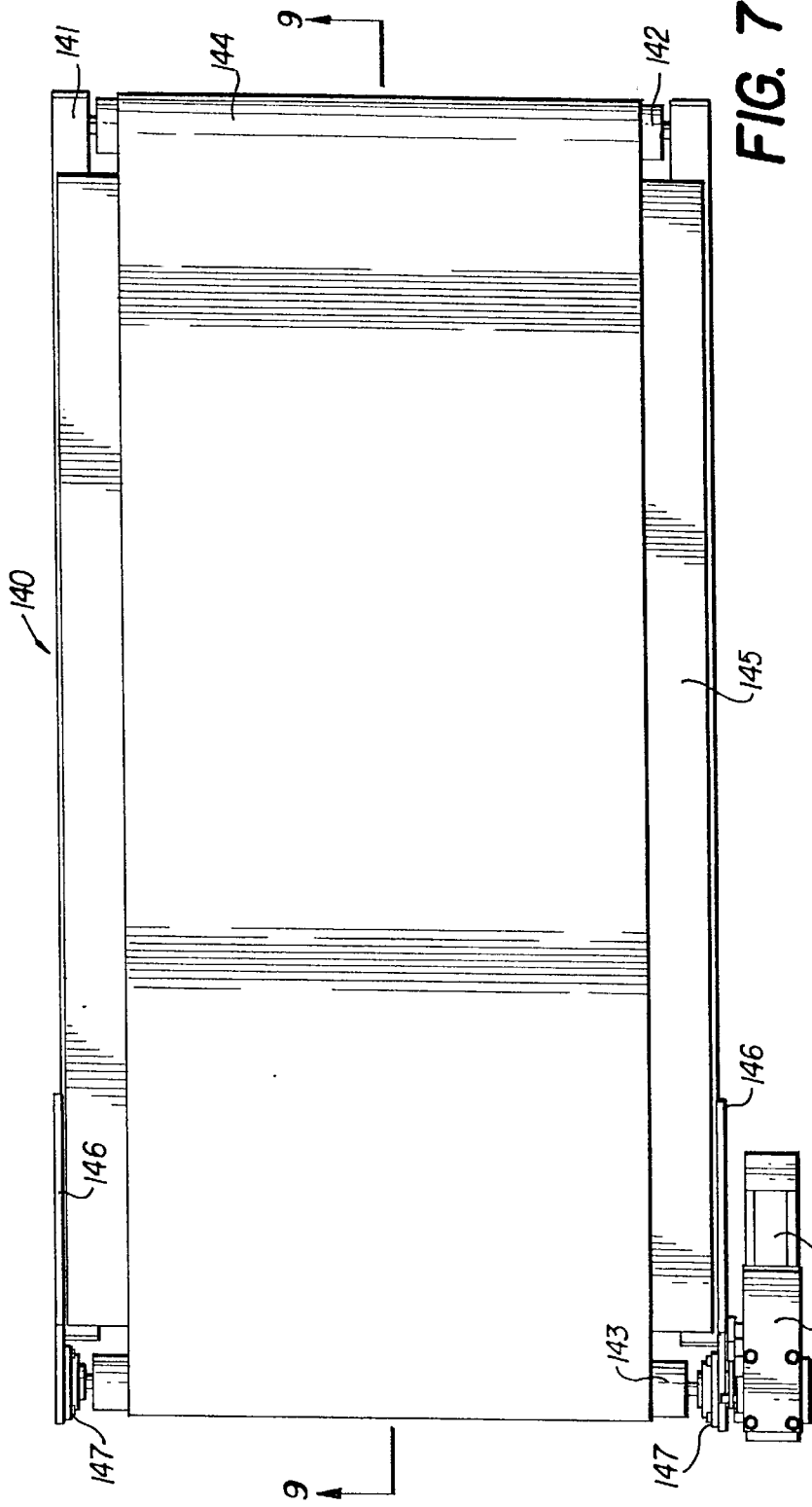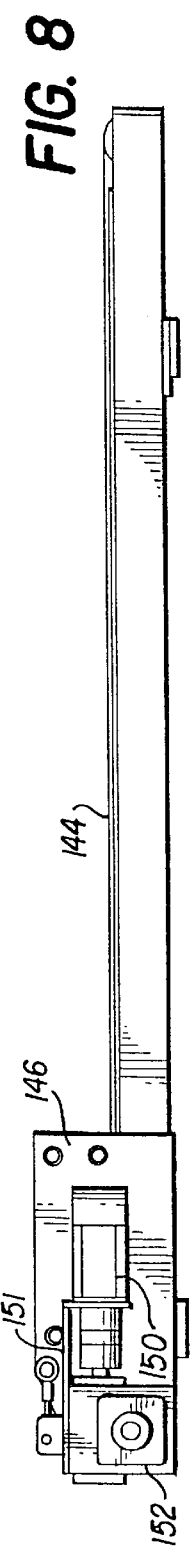

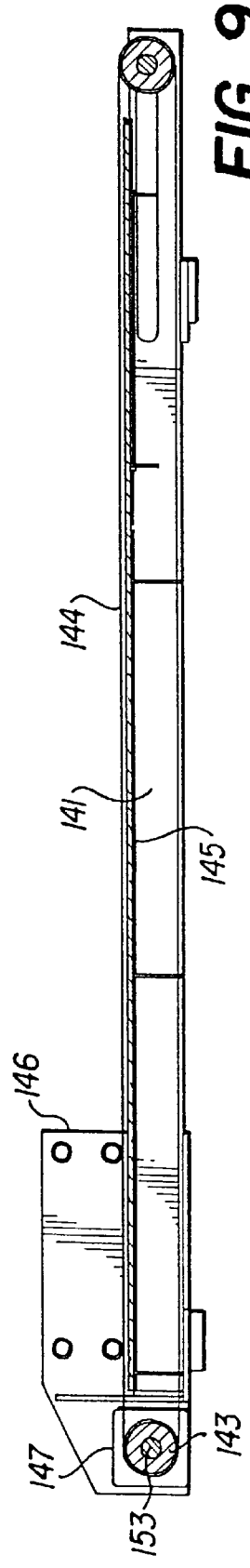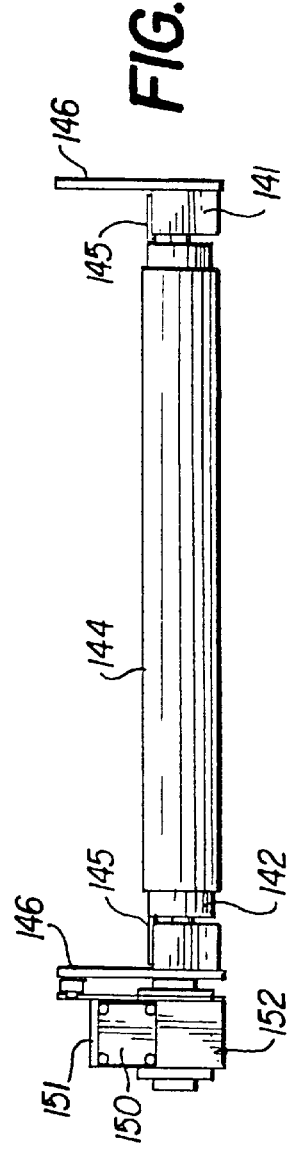

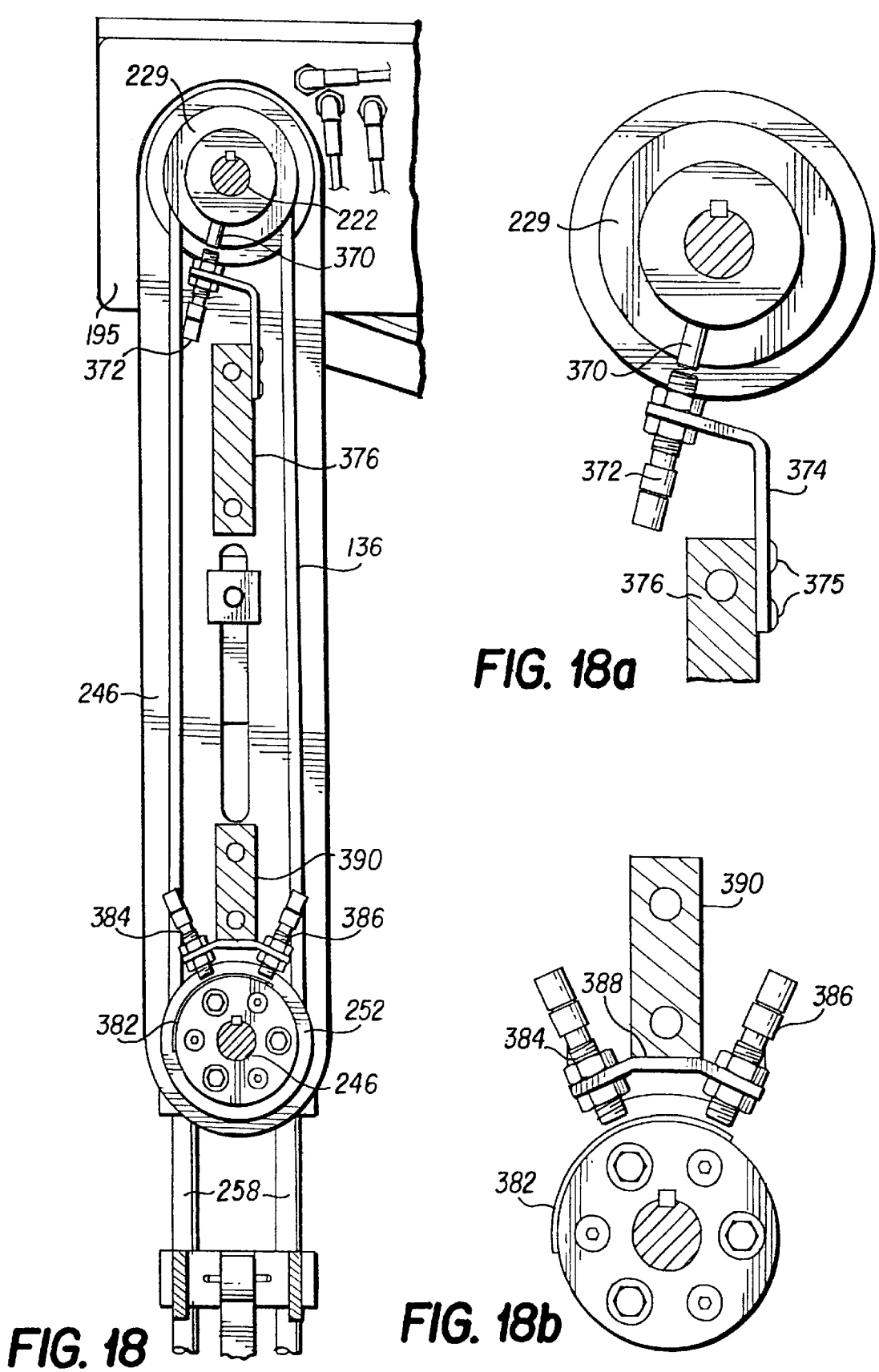

POWERED GAIT ORTHOSIS AND METHOD OF UTILIZING SAME

This application claims the priority of U.S. Provisional Application No. 60/227,597, filed Aug. 25, 2000.

BACKGROUND OF THE INVENTION

The present invention relates to a powered gait orthosis, and more particularly to a device to aid in research and rehabilitation of non-ambulatory patients and provide therapeutic exercise for those with spinal cord injuries, neurological impairments and those recovering from orthopedic procedures. The invention also enables the measurement of outcomes and records patient session data for progress analysis.

Prior art devices for similar purposes are often not of sanitary construction and may require special electrical power sources and excessive site preparation. Additionally, such devices may be difficult to ship and setup. The prior art often requires the presence of more than one trained operator, thereby increasing the cost of such therapy. Additionally, therapists often perform portions of the therapy manually which does not result in uniform reproducible therapy to the patient. Prior art devices do not always provide easy patient access, and the devices may not successfully simulate a natural walking motion in the patients legs.

SUMMARY OF THE INVENTION

The present invention is of sanitary construction since it utilizes components formed of steel and aluminum. The components are shipped in disassembled arrangement, and are then bolted together on site, thereby facilitating shipping and setup of the device. The devices is self-contained and free standing, requiring only common electrical power sources and minimal site preparation. A single technician is required to operate the invention. When a patient is properly position and attached to the device, movement of the legs is performed robotically by the device, and no manipulation of a patient's leg by a technician or therapist is required. However, the technician operating the device can adjust the operation of the components thereof in accordance with the requirements of different patients. The device has been successful in simulating a natural walking motion in legs of patients.

A powered lifting device is provided for lifting a patient from a wheelchair and transporting him to a position over a treadmill, whereupon he may be lowered onto the treadmill. Similar leg actuator assemblies are disposed at opposite sides of the treadmill, each assembly including a support arm which is pivoted for movement away from the treadmill to facilitate access to the treadmill. Each support arm pivotally supports a first depending arm from which a second depending arm is pivotally supported. A pair of servo motors are supported by each support arm and are drivingly connected to the first and second depending arms to independently move the depending arms about the pivot axes thereof. A first attachment means is adjustably carried by the first depending arm for attachment to a patient's leg just above the knee; and a second attachment means is adjustably carried by the second depending arm for attachment of a patient's leg at the ankle.

Each of the support arms is vertically adjustable independently of the other. The attachment means on the first and second depending arms are vertically and horizontally adjustable relative to the depending arm on which they are mounted. A control means includes a computer electrically connected to the drive means for the treadmill and the servo motors which operate the first and second depending arms so that the treadmill as well as the depending arms at opposite sides of the treadmill will operate in a coordinated manner to cause the legs of the a patient to move in a desired gait. Connected to the computer is an operator friendly touch screen interface with the ability to input, monitor and record pertinent data.

Sensor means is also provided for sensing the home position of each second depending arm and for sensing over-travel of such second depending arms and the knee joints of the device to thereby prevent damage to the knees of a patient. Locking devices are provided for locking the powered lifting means in position and for locking the support arms in position. The lifting means also includes load cells for measuring the weight of a patient suspended thereby.

When using the invention, a patient is initially fitted with a special harness and is lifted from a wheelchair to a standing position where weight is measured. A database containing individual set-up and historical information will be displayed on the touch screen. The patient is then moved over the treadmill and lowered thereon. The gait assist mechanisms are then attached to one or both legs of the patient. The percent of supported body weight can be adjusted as required as muscle strength of the patient develops. All component speeds are synchronized and controlled by operator input with treadmill speeds ranging from 0 to 2 mph. During a session, information such as blood pressure, heart rate, blood oxygen content, treadmill speed, session duration, etc. can be displayed and recorded for further analysis.

BRIEF DESCRIPTION OF THE DRAWINGS

FIG. 1 is a side view of the invention showing a patient in a wheelchair prior to being lifted therefrom;

FIG. 6b is a sectional view taken on line 6b–6b of FIG. 6a;

FIG. 7 is a top view of the treadmill of the invention;

FIG. 8 is a side view of the treadmill;

FIG. 9 is a sectional view taken along line 9—9 of FIG. 7;

FIG. 10 is an end view of the treadmill;

FIG. 18 is an enlarged sectional view taken along line 18—18 of FIG. 15;

FIG. 18a is an enlarged view of a portion of the structure shown in FIG. 18;

FIG. 18b is an enlarged view of another portion of the structure shown in FIG. 18;

DESCRIPTION OF THE PREFERRED EMBODIMENT

Figure 1A:
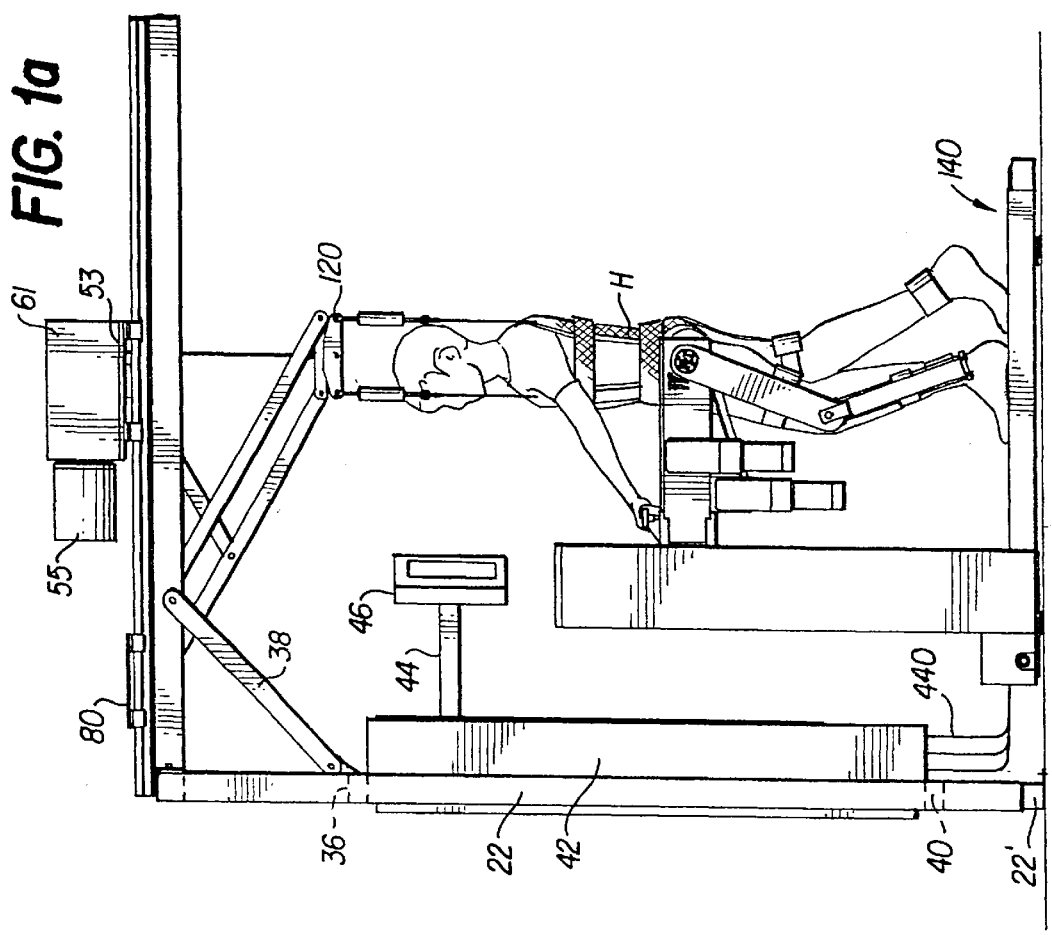
FIG. 1a is a side view showing a patient after having been lowered onto the treadmill of the invention.
Figure 2:
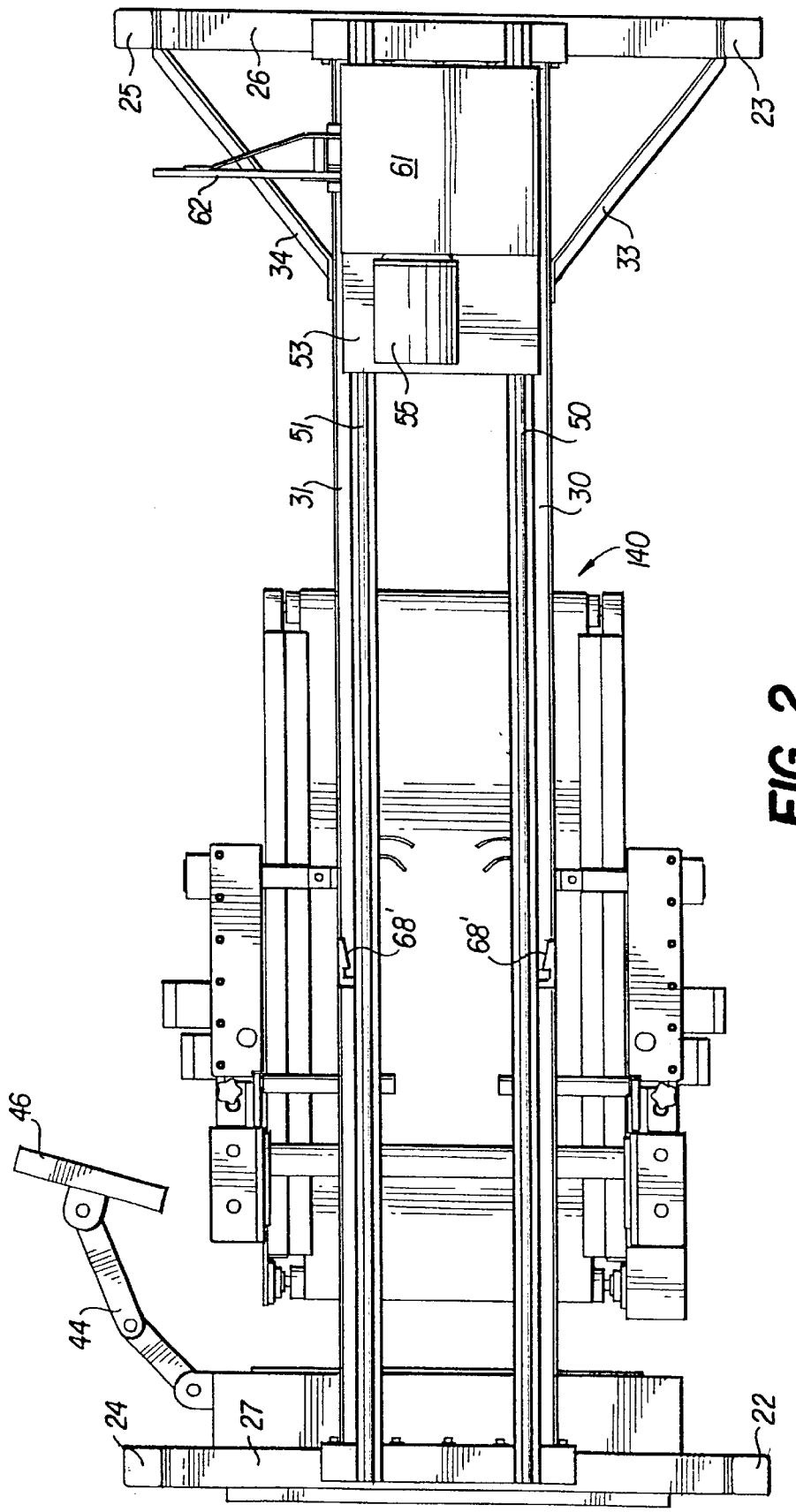
FIG. 2 is an enlarged top view of the structure shown in FIG. 1.
Figure 3:
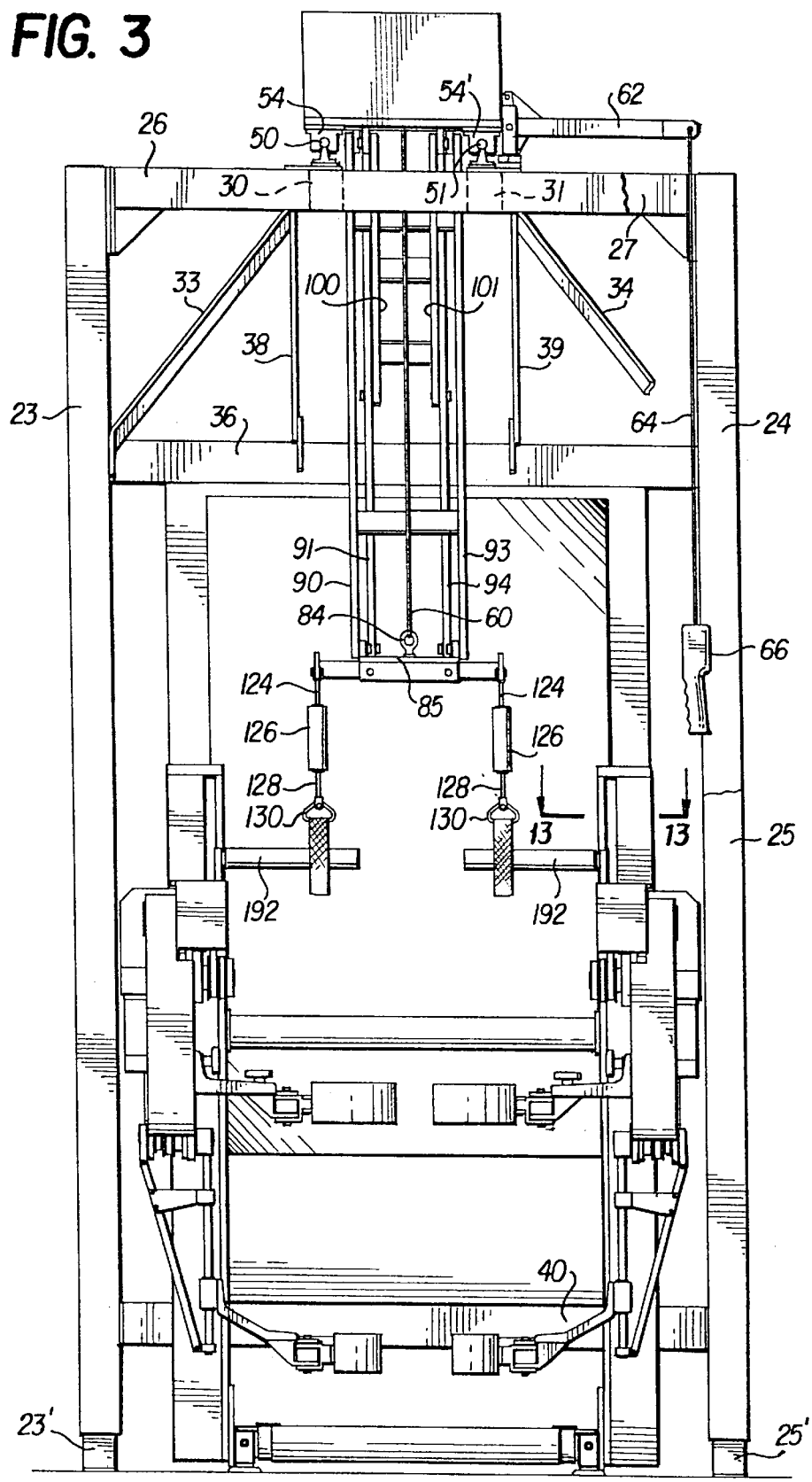
FIG. 3 is an enlarged end view, partially broken away, of the structure shown in FIG. 1 looking at the right side thereof.

Referring now to the drawings wherein like reference numerals designate corresponding parts throughout the several views, FIGS. 1, 1a, 2 and 3 illustrate a rigid framework support structure formed preferably of steel including four upright beams 22, 23, 24 and 25 having base portions 22', 23' which are visible in FIGS. 1 and 25' which is visible in FIG. 3, a corresponding base portion being provided at the bottom of beam 24. These base portions may be bolted to a supporting surface to secure the beams in fixed position. A first cross beam 26 is connected at opposite ends as by bolting to the upper ends of beams 23 and 25; and a cross beam 27 is similarly connected at opposite ends to the upper ends of beams 22 and 24.

Longitudinally extending beams 30 and 31 have the opposite ends thereof secured as by bolting to cross beams 26 and 27. A first brace member 33 has the opposite ends thereof connected as by bolting to beam 23 and beam 30. A second brace member 34 has the opposite ends thereof connected as by bolting to beam 25 and beam 31. A cross beam 36 has the opposite ends thereof connected as by bolting to beams 22 and 24. A third brace member 38 has the opposite ends thereof connected as by bolting to cross member 36 and beam 30; and a fourth brace member 39 has the opposite ends thereof similarly connected to cross beam 36 and beam 31. A further cross beam 40 has the opposite ends thereof connected as by bolting to beams 22 and 24.

A control panel 42 is supported between cross beams 36 and 40, and a mirror 43 is supported on the right hand face of the panel as seen in FIG. 1 so that a patient may see himself when in position on the treadmill hereinafter described. A pivoted linkage 44 adjustably supports a touch screen 46 from the control panel.

Figure 4:
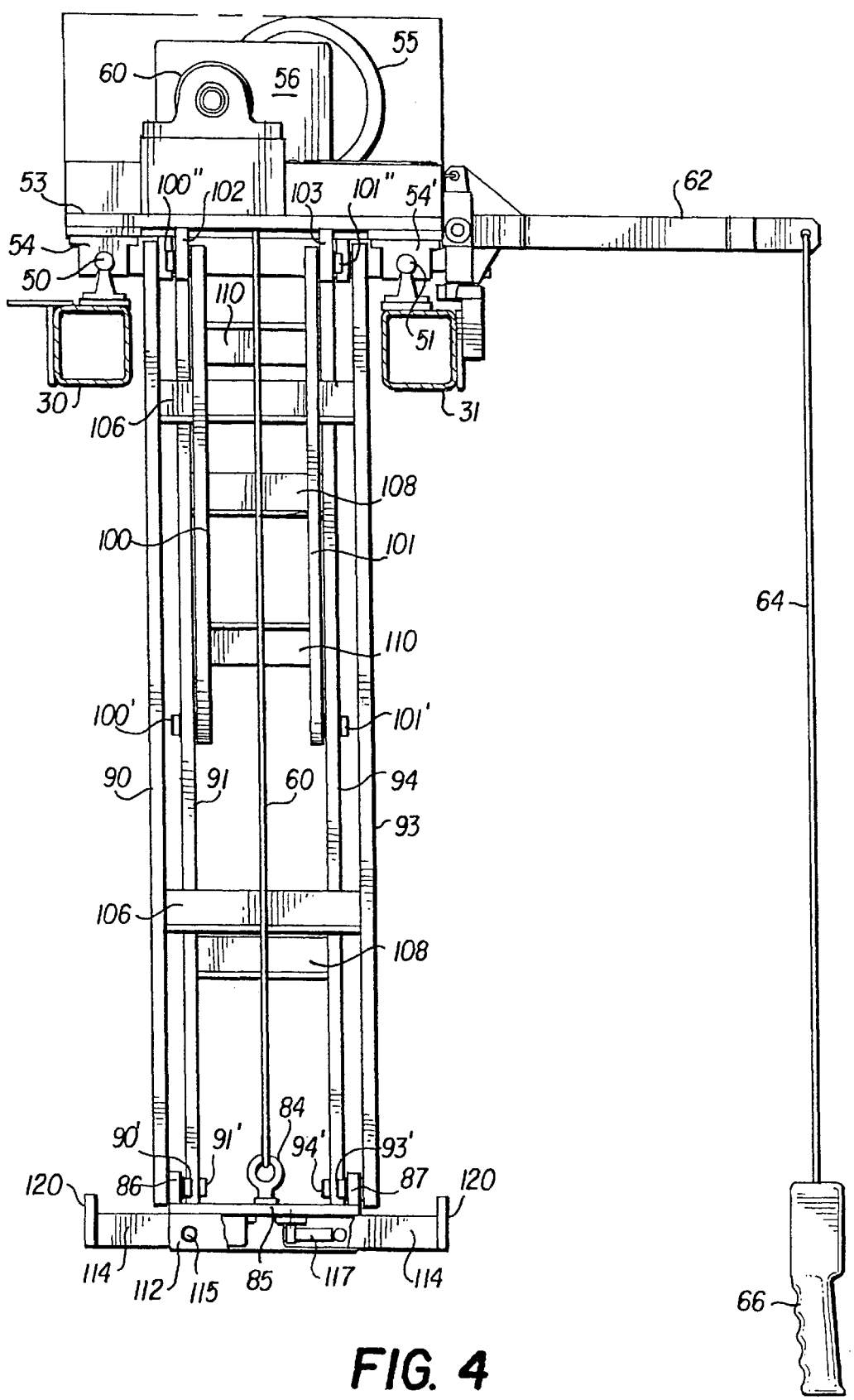
FIG. 4 is an enlarged view of a portion of the structure shown in FIG. 3 with certain elements removed for the sake of clarity.

A pair of longitudinally extending rails 50 and 51 are secured as by bolting to the upper surfaces of beams 30 and 31. As seen in FIGS. 1, 3, 5 and 6, the lifting means includes a winch frame 53 which is slidably supported on rail 50 by a pair of spaced linear bearings 54 and is also slidably supported on rail 51 by a further pair of similar bearings 54'. Mounted on winch frame 53 are a winch motor 55 the output of which is connected through a gear box 56 and a coupling 57 to a reel 58 having a cable 60 wound thereon. A cover 61 is shown in FIG. 1 over some of the winch components. A lever 62 is pivotally supported on winch frame 53. A pendant 64 is connected to the outer end of the lever and the pendant hangs downwardly as seen in FIGS. 3 and 4 with the lower end thereof connected to a hand grip 65. The handgrip includes an operating control means for energizing and de-energizing the winch motor. Additionally, the hand grip can be used for releasing the locking mechanism associated with the winch frame as hereinafter described.

Figure 6:
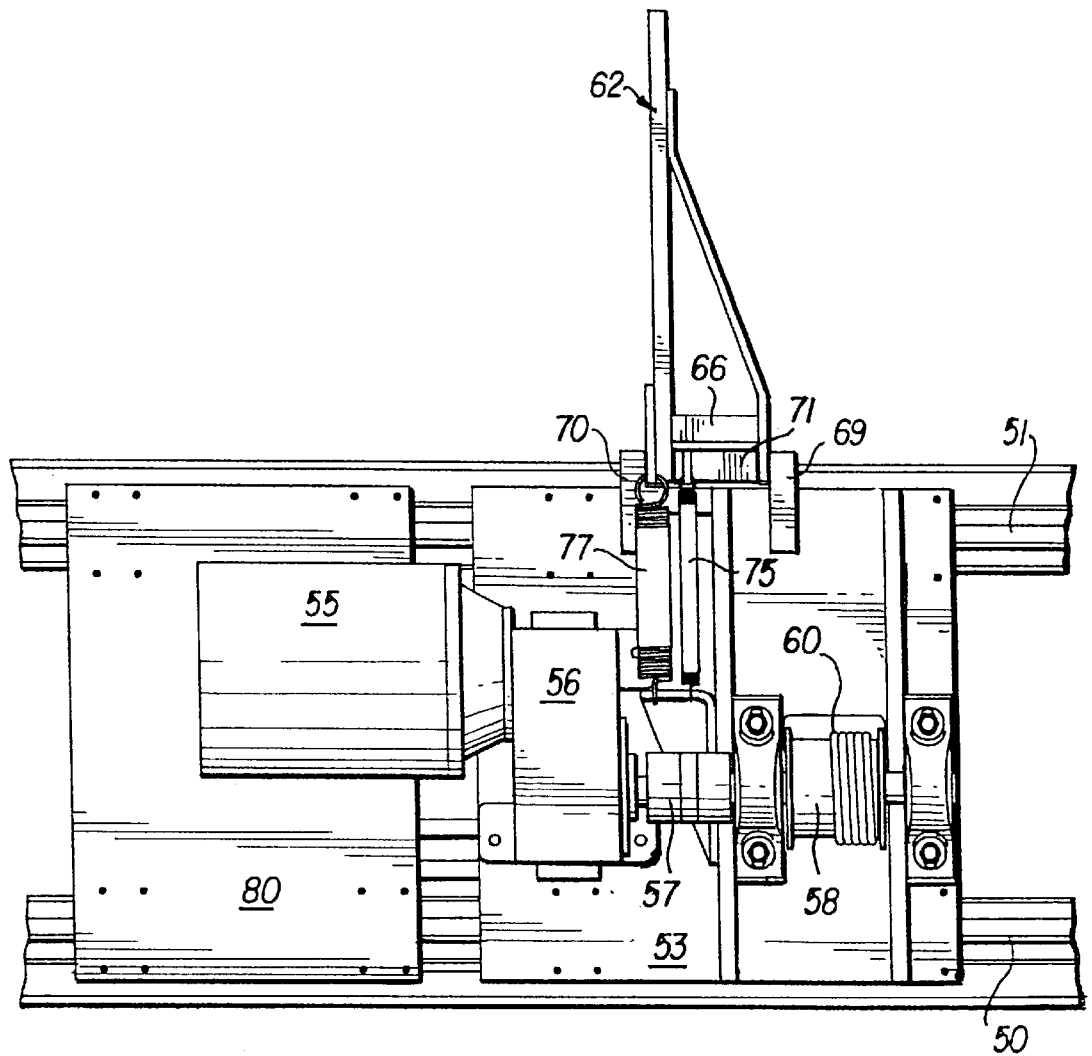
FIG. 6 is an enlarged top view of the powered lifting means of the invention.
Figure 6A:
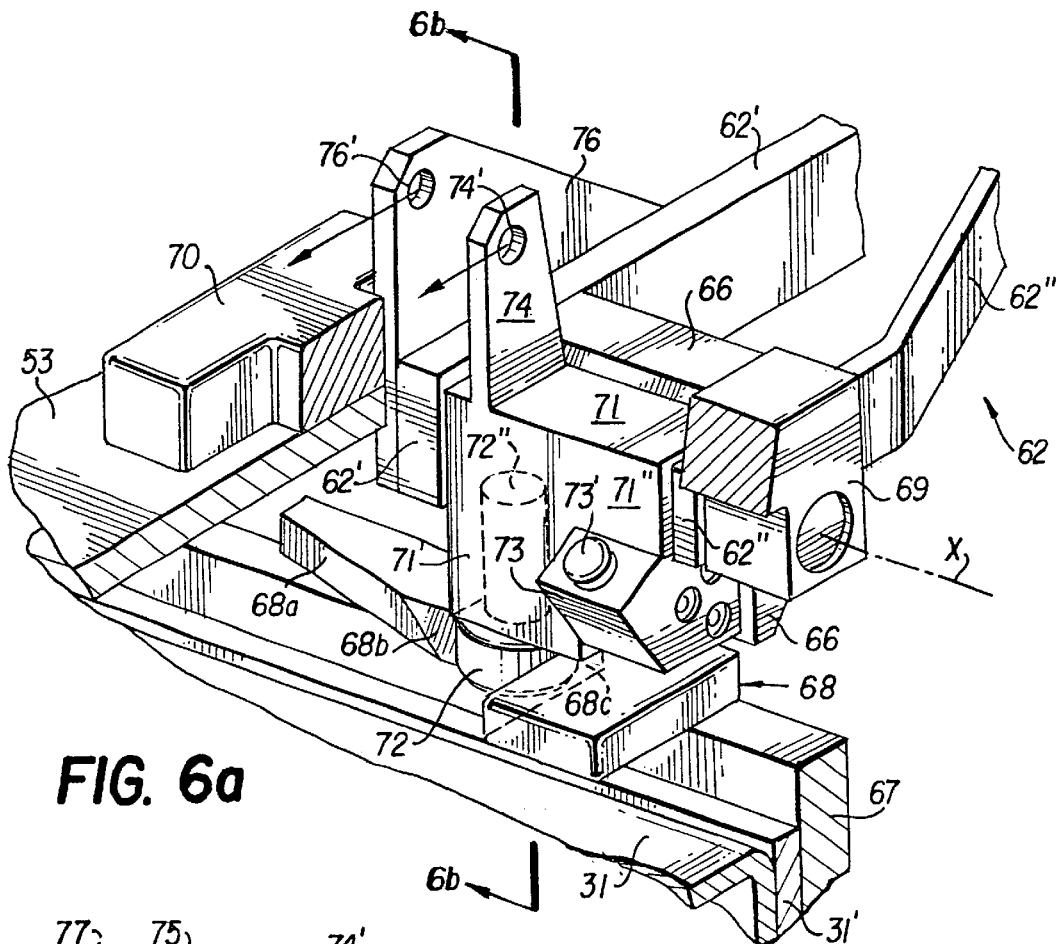
FIG. 6a is an enlarged top perspective view of the locking means for the winch frame.
Figure 6B:
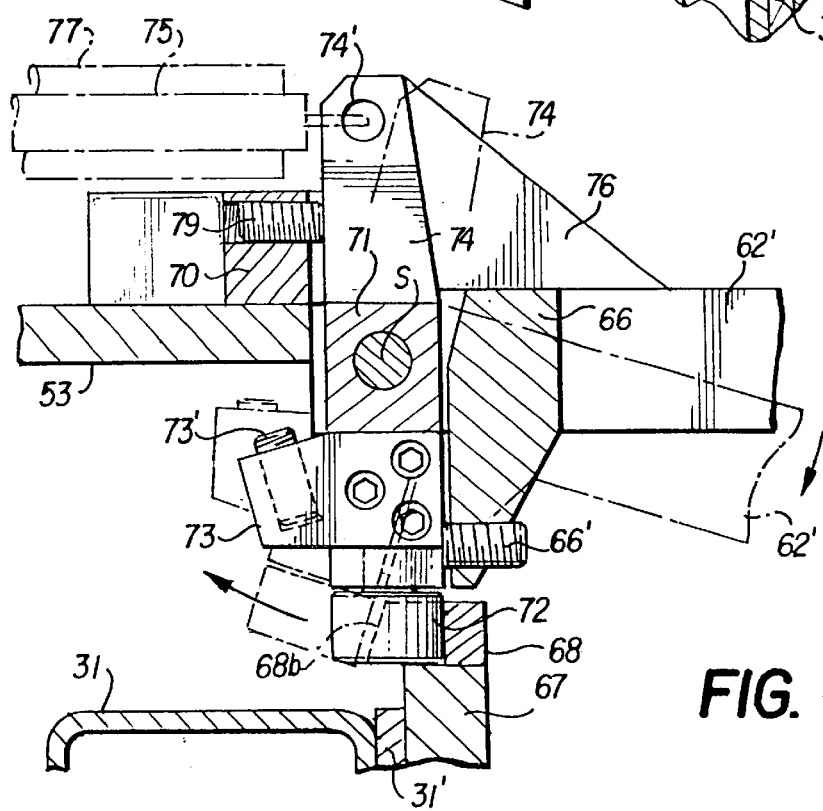

Referring to FIGS. 6a and 6b, the locking means for lever 62 is illustrated. Lever 62 includes spaced arms 62' and 62" with a spacer block 66 disposed between the ends thereof and connected thereto as by bolting. Spacer block 66 has an adjustment set screw 66' threaded into a threaded bore provided through the spacer block. Beam 31 has a plate 31' secured thereto as by bolting, and a stop mount 67 is secured as by bolting to plate 31'. A travel stop 68 is secured as by machine screws to stop mount 67 and includes a first cam surface 68a joining a second cam surface 68b which joins with a recess 68c. The travel stop is shown which is mounted at the right-hand portion of the invention device as seen in FIGS. 1 and 2. A further travel stop 68' is provided for locking the winch frame in position over the treadmill, stop 68' being a mirror image of travel stop 68.

A pair of spaced support blocks 69 and 70 are carried by winch frame 53 and support opposite ends of a shaft S fixed within holes in the blocks. A lock pivot member 71 is of generally L-shaped configuration including a downwardly extending portion 71' and a laterally extending portion 71". A cam roller 72 is mounted on a shaft 72' which is fixed within a hole formed in portion 71' whereby the cam roller is carried by lock pivot member 71. A lock arm stop 73 is mounted on portion 71' of the lock pivot member 71 by machine screws. An adjustment set screw 73' is threaded into a threaded hole formed through lock arm stop 73.

An integral spring mount 74 extends upwardly from the top of lock pivot member 71 and has a hole 74' formed therethrough which receives one end of a first tension spring 75. A further spring mount 76 is secured to lever arm 62' as by bolting and has a hole 76' formed therethrough which receives one end of a second tension spring 77. As seen in FIG. 6, the opposite ends of springs 75 and 77 are connected to a bracket 78 secured as by bolting to the winch frame 53. The springs will exert a continuous force on the upper ends of spring mounts 74 and 76 urging the lock pivot member 71 and the lever arm 62 to rotate counterclockwise about the axis X of shaft S. Such rotation of member 71 is prevented by contact of roller 72 with the wall of recess 68c. Such rotation of the lever arm is prevented by contact of spring mount 76 with a set screw 79 threaded into a threaded hole formed in support block 70.

As the winch frame moves along rails 50 and 51; between the travel stops, cam roller shaft 72' is disposed substantially vertically because of engagement of set screw 66' with member 71. When roller 72 comes into contact with cam surfaces 68a and 68b, lock pivot member 71 is rotated in a clockwise direction about axis X and then rides into recess 68c where it is held in place by the tension of spring 75 to thereby lock the winch frame in position. At this time, lever 62 is held in a horizontal position under the influence of spring 77.

When it is desired to unlock the winch frame in order to move it to a different position, an operator pulls down on lever 62 causing spacer block 66 to move in a clockwise direction relative to axis X. Set screw 66' then causes member 71 to move in a clockwise direction about axis X which causes roller 72 to move out of recess 68*c* whereupon the winch frame can be moved along its supporting rails and the roller 72 moves out of engagement with cam surfaces 68*b* and 68*a*.

Figure 5:
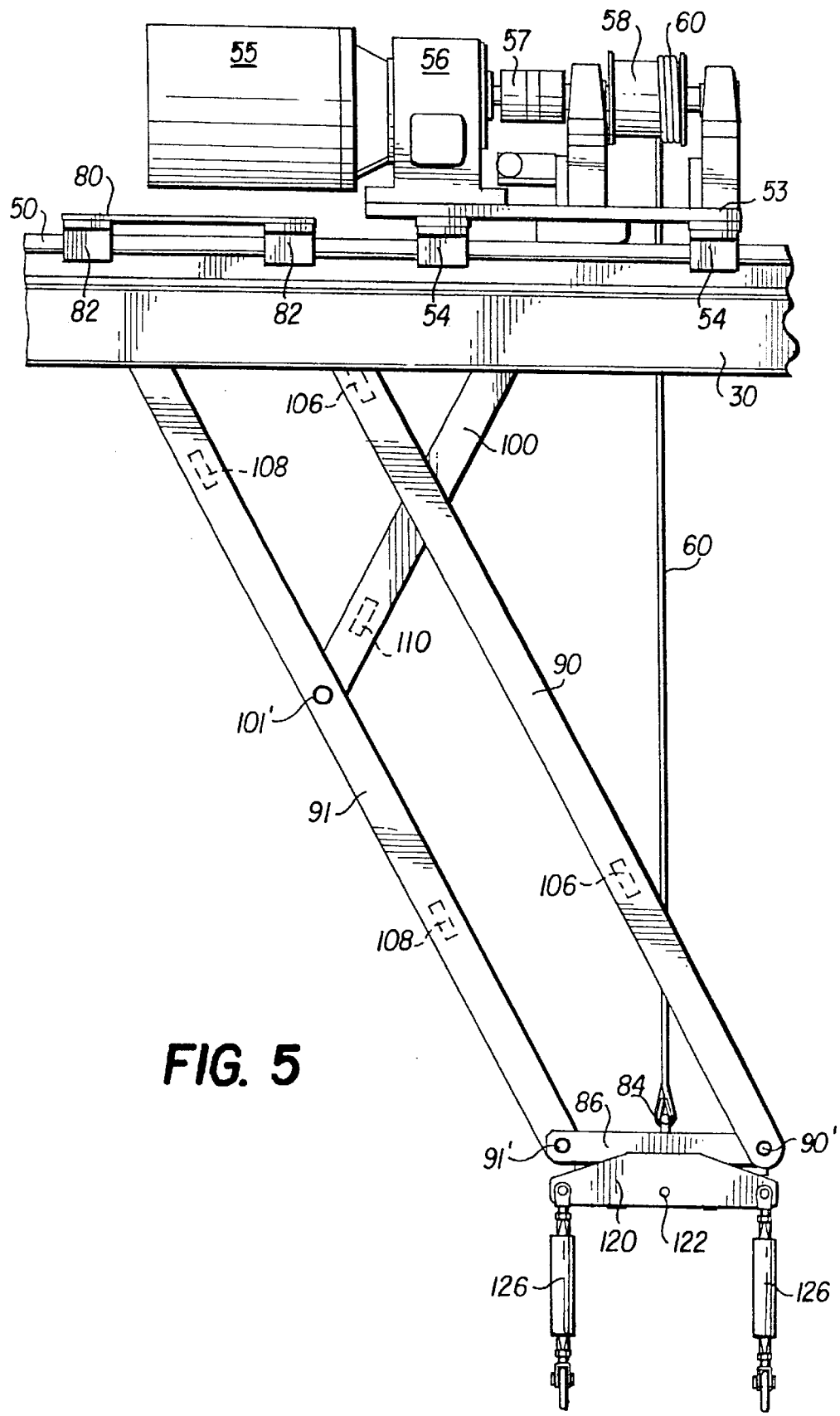
FIG. 5 is an enlarged view of a portion of the structure shown in FIG. 1 illustrating the parallelogram linkage of the lifting means.

As seen in FIGS. 3–5, the lifting means also includes a trolley frame 80 supported by two linear bearings 82 slidably mounted on rail 50, it being understood that two additional similar bearings are slidably mounted on rail 51. The lower end of cable 60 is connected by an eye bolt 84 connected to a plate 85. Rigidly secured as by bolting to the upper surface of plate 85 are two spaced similar elongated members 86 and 87. A parallelogram connection is provided between plate 85 and the winch frame 53 as well as the trolley 80 including a first pair of links 90 and 91 having the lower ends thereof pivotally connected to opposite ends of member 86 at points 90' and 91' respectively. The upper ends of links 90 and 91 are pivotally connected to the trolley frame 80. A second pair of links 93 and 94 are disposed parallel with links 90 and 91 and are pivotally connected at their lower ends to opposite ends of member 87 at points 93' and 94' in the same manner that links 90 and 91 are connected to member 86. The upper ends of links 93 and 94 are pivotally connected to the trolley frame 80.

A further pair of links 100 and 101 are pivotally connected at their lower ends to intermediate portions of links 91 and 94 respectively at points 100' and 101'. The upper ends of links 100 and 101 are connected to lugs 102 and 103 respectively at points 100" and 101". A pair of cross members 106 are connected between facing surfaces of links 90 and 93 at spaced points along the links. A pair of cross members 108 are connected between facing surfaces of links 91 and 94 at spaced points along the links. A pair of cross members 110 are connected between facing surfaces of links 100 and 101 at spaced points along the links.

As seen in FIG. 4, a housing 112 is secured as by bolting to the undersurface of plate 85 and supports a pair of similar arms 114 which extend laterally from the housing and are pivotally mounted at points 115 for pivotal movement relative to the housing. Load cells 117 are supported within the housing and are in contact with the inner ends of arms 114 for measuring the weight of a patient suspended from arms 114. The outputs of the load cells provide electrical signals which may be suitably recorded.

As seen in FIGS. 3–5 similar plates 120 are supported at the outer ends of arms 114 for pivotal movement about the pivotal axes 122 thereof. Four threaded rods 124 have the upper ends thereof pivotally secured to opposite ends of plates 120, the lower end of each of said rods being threaded into the open upper end of a cylinder 126. The lower end of each cylinder 126 is open and is internally threaded to receive a threaded rod 128 the lower end of which is connected to a D-ring connector 130. Each cylinder 126 is threaded in opposite directions at the opposite open ends thereof so that when cylinder 126 is rotated, the threaded rods and cylinder act as a turnbuckle to pull rods 124 and 128 toward one another or away from one another depending on the direction of the cylinder.

Each of the D-rings is adapted to be connected with a strap 132 forming part of a harness H secured to the torso of a patient as seen in FIGS. 1 and 1*a*. When a patient arrives in a wheelchair, the harness H is attached to the D rings. The winch of the lifting means is activated by use of the control means on hand grip 66 and the winch raises the patient vertically upward. As the patient rises, the parallelogram linkage ensures that the patient is supported in a generally vertical or standing position. As the patient rises, trolley frame 80 moves away from the winch frame into the position shown in FIG. 1*a*. When the patient has been raised to the desired height from the wheelchair, the patient is moved manually to move the winch frame and trolley frame longitudinally of the device and then lowered into the position shown in FIG. 1*a* where his feet are supported by the treadmill.

Referring to FIGS. 7–10, the treadmill 140 of the invention is shown. The treadmill includes a frame 141 rotatably supporting rollers 142 and 143 at opposite ends thereof. A belt 144 is trained around the rollers in a conventional manner, and the usual deck assembly 145 is provided. A pair of plates 146 are connected to opposite sides of the frame of the treadmill as by bolting for a purpose hereinafter described. The roller 143 is rotatably supported at opposite ends thereof by a pair of similar bearings 147 mounted as by bolting on plates 146. A servo motor 150 is supported by a bracket 151 connected to a gear box 152 drivingly connected to shaft 153 of roller 143 as seen in FIG. 9.

Figure 11:
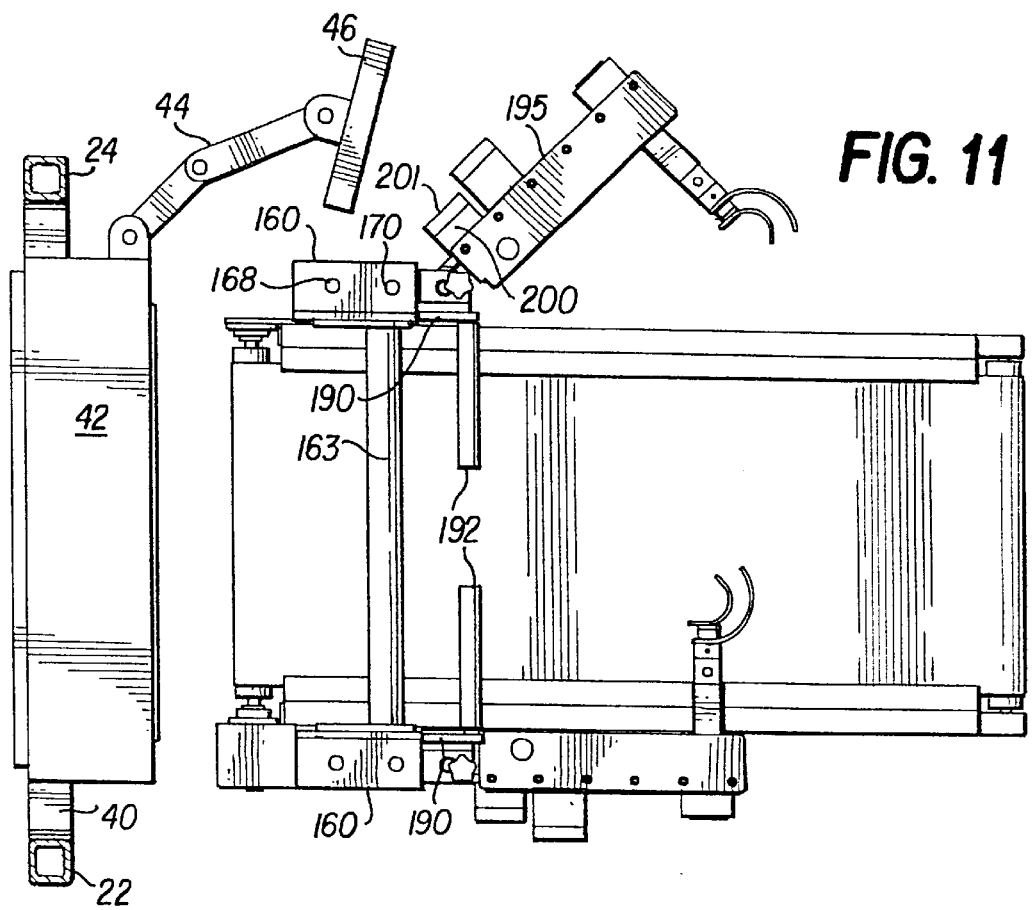
FIG. 11 is a top view of the device with the support structure removed.

As seen in FIG. 11, a pair of housings 160 are disposed at opposite sides of the treadmill and are connected to the treadmill as by bolting to plates 146 which are connected to opposite sides of the treadmill frame. A cross member 163 has the opposite ends thereof connected as by bolting to the facing inner surfaces of housings 160. The two housings and the components supported thereby are of similar construction, one being the mirror image of the other, and accordingly, a single housing is described hereinafter, it being understood the description of the details of construction of one housing and the components supported thereby is equally applicable to both of the housings with similar components of both housings being given the same reference numerals.

Figure 13:
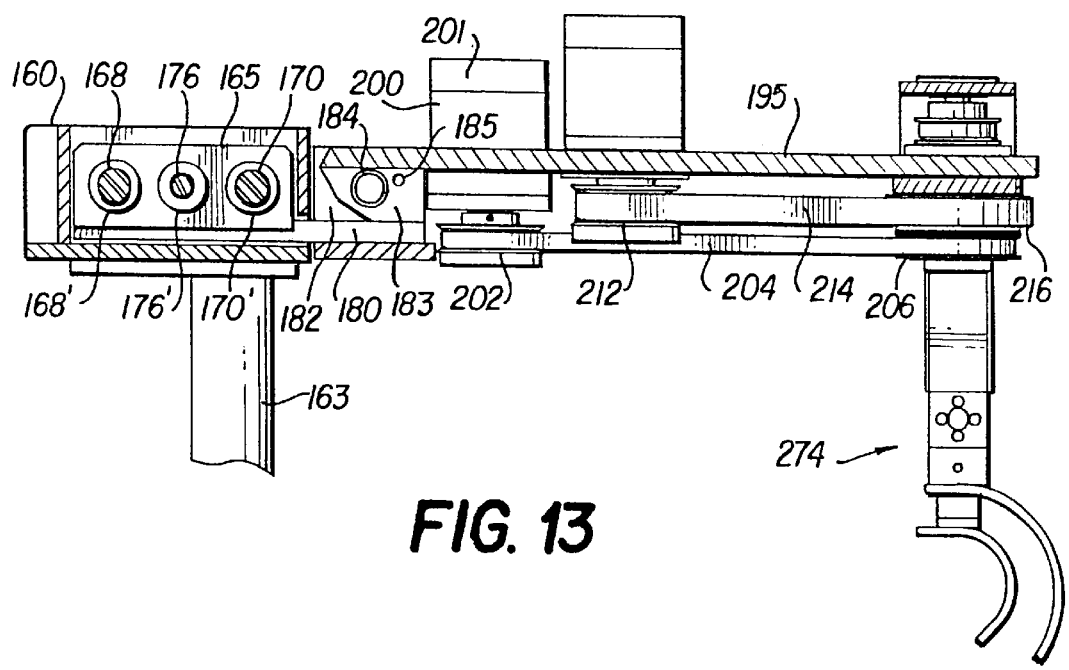
FIG. 13 is sectional view taken along line 13—13 of FIG. 3.
Figure 12:
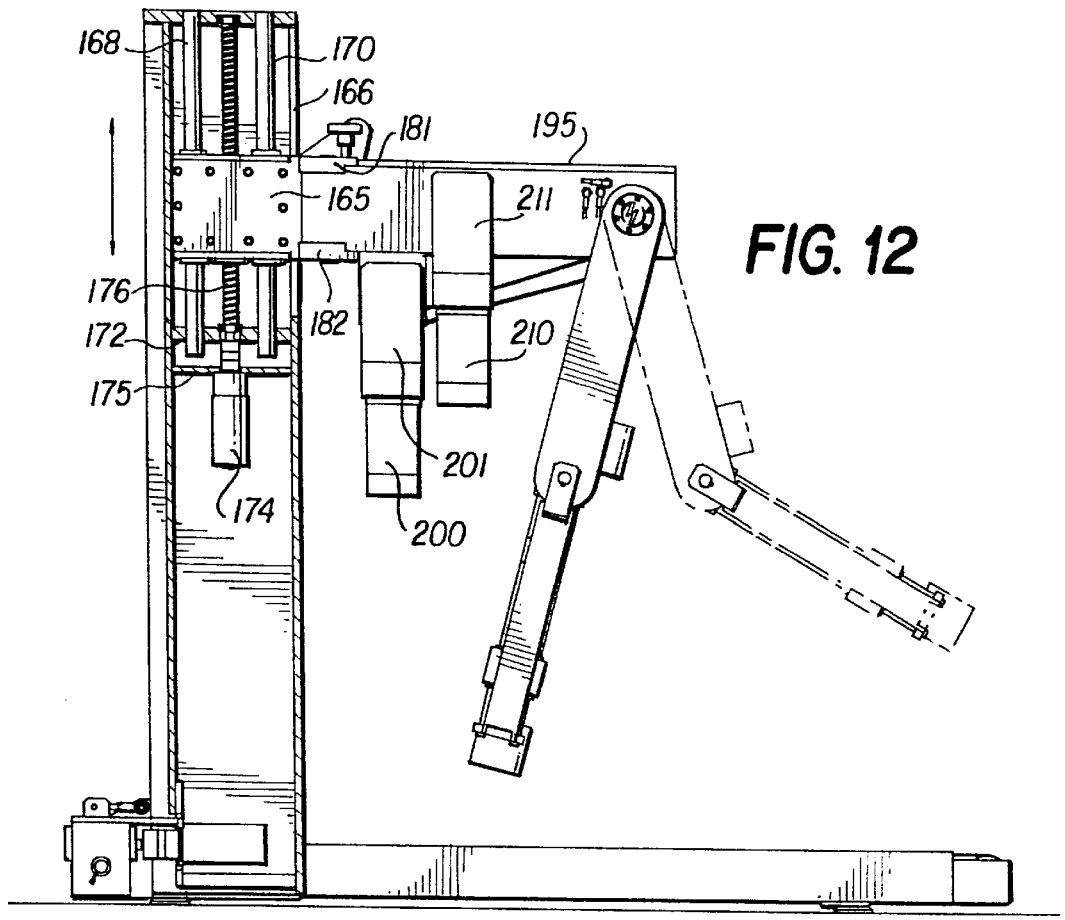
FIG. 12 is a side view of a housing at one side of the treadmill and the structure supported thereby with one side panel of the housing removed for the sake of clarity.

As seen in FIG. 12, housing 160 appearing at the bottom of FIG. 11 is shown with a side panel thereof removed. A carriage 165 is vertically movable within housing 160 and extends through a slot 166 disposed in one side of the housing. Two guide rods 168 and 170 are disposed within the housing with their upper ends fixed to the top member of the housing and with the lower ends fixed to a cross member 172 extending between and connected to opposite sides of the housing. As seen in FIG. 13, the guide rods extend through linear bearings 168' and 170' supported by the carriage so that the carriage is guided in its vertical movement within the housing. A 24 volt permanent magnet motor 174 is supported by a cross member 175 extending between and connected to opposite sides of the housing. The output of motor 174 is connected to a lead screw 176 that is threaded through a threaded bushing 176' supported by the carriage whereby rotation of the lead screw will cause vertical movement of carriage 165 along guide rods 168 either in an upward or downward direction depending of the direction of rotation of the lead screw.

As seen in FIGS. 12 and 13, carriage 165 is rigidly connected as by bolting to member 180. An upper plate 181 and a spaced lower plate 182 are attached as by bolting to member 180. The upper plate 180 has been removed from FIG. 13 for the sake of clarity. A block 183 is secured as by bolting to a support arm 195 and receives a pivot pin 184 which extends therethrough and is fixed thereto, the upper and lower ends of the pivot pin being supported in bushings (not shown) in plates 181 and 182 respectively whereby support arm 195 is mounted for swinging movement outwardly of the treadmill.

A hole 185 is formed in the upper surface of block 183 and is adapted to cooperate with a locking device 186 which comprises a hand knob having a threaded stem the lower end of which is not threaded and is adapted to be received in hole 185 to lock the support arm in its operative position as shown in the lower portion of FIG. 11. The threaded portion of the stem of the locking device is received within a suitable threaded hole formed in the upper plate 180. When it is desired to release the locking device, it is simply unthreaded to the point where the lower end of the stem of the locking device clears hole 185, whereupon support arm 195 can be swung outwardly. When the support arm is subsequently swung inwardly; the holes in the upper plate and block 183 are aligned with one another whereupon the locking device can be threaded downwardly to cause the lower end of the stem to again enter hole 185 so that the support arm is locked in operative position.

A plate 190 is secured as by bolting to plate 180 and supports an inwardly extending hand hold 192. As seen in FIGS. 3 and 11, hand holds 192 extend inwardly toward one another in position to be readily grasped by a patient when the patient is supported over the threadmill.

Figure 14:
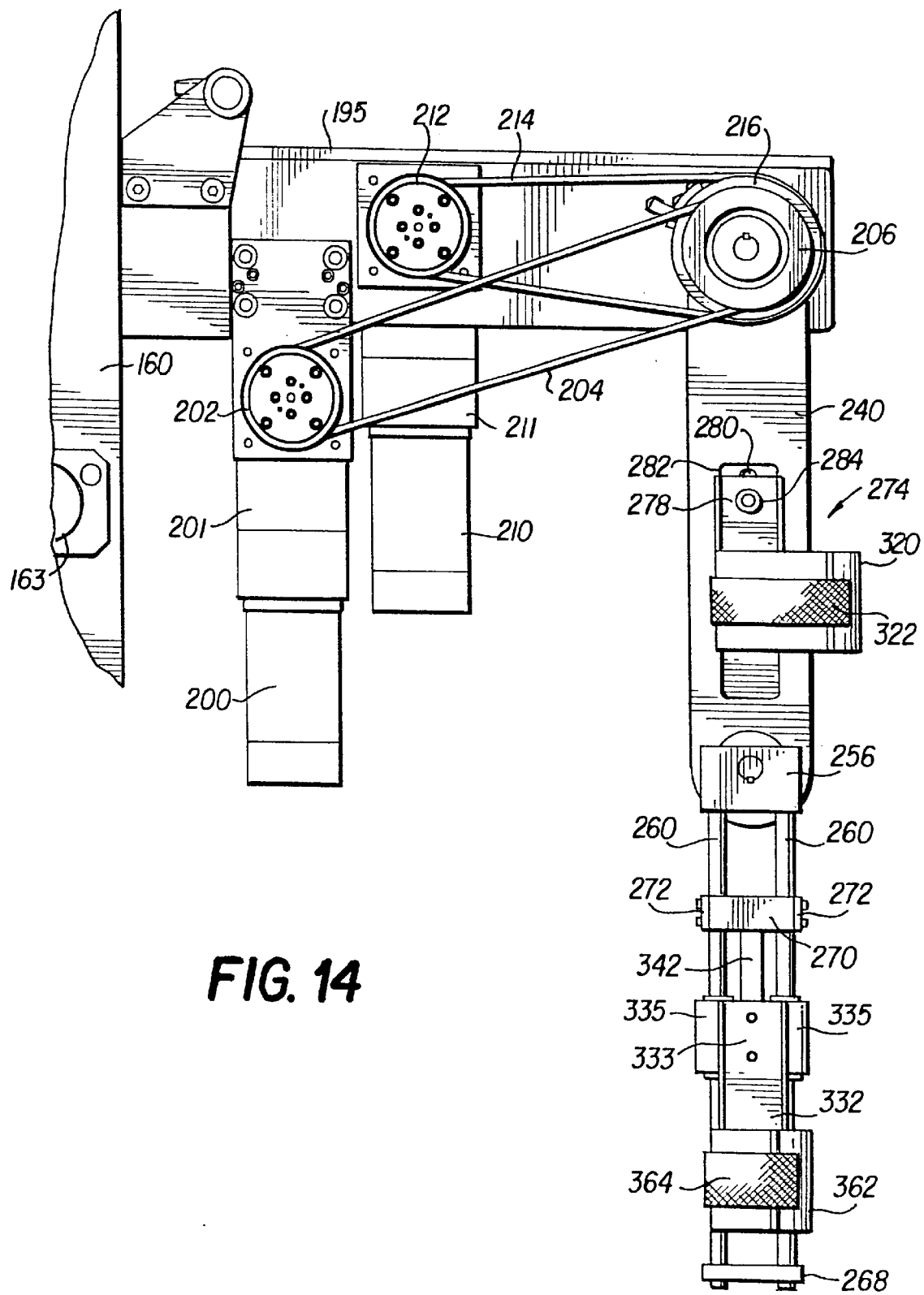
FIG. 14 is a side view of the support arm of FIG. 13 with covers for the servo motor pulleys removed for the sake of clarity.
Figure 15:
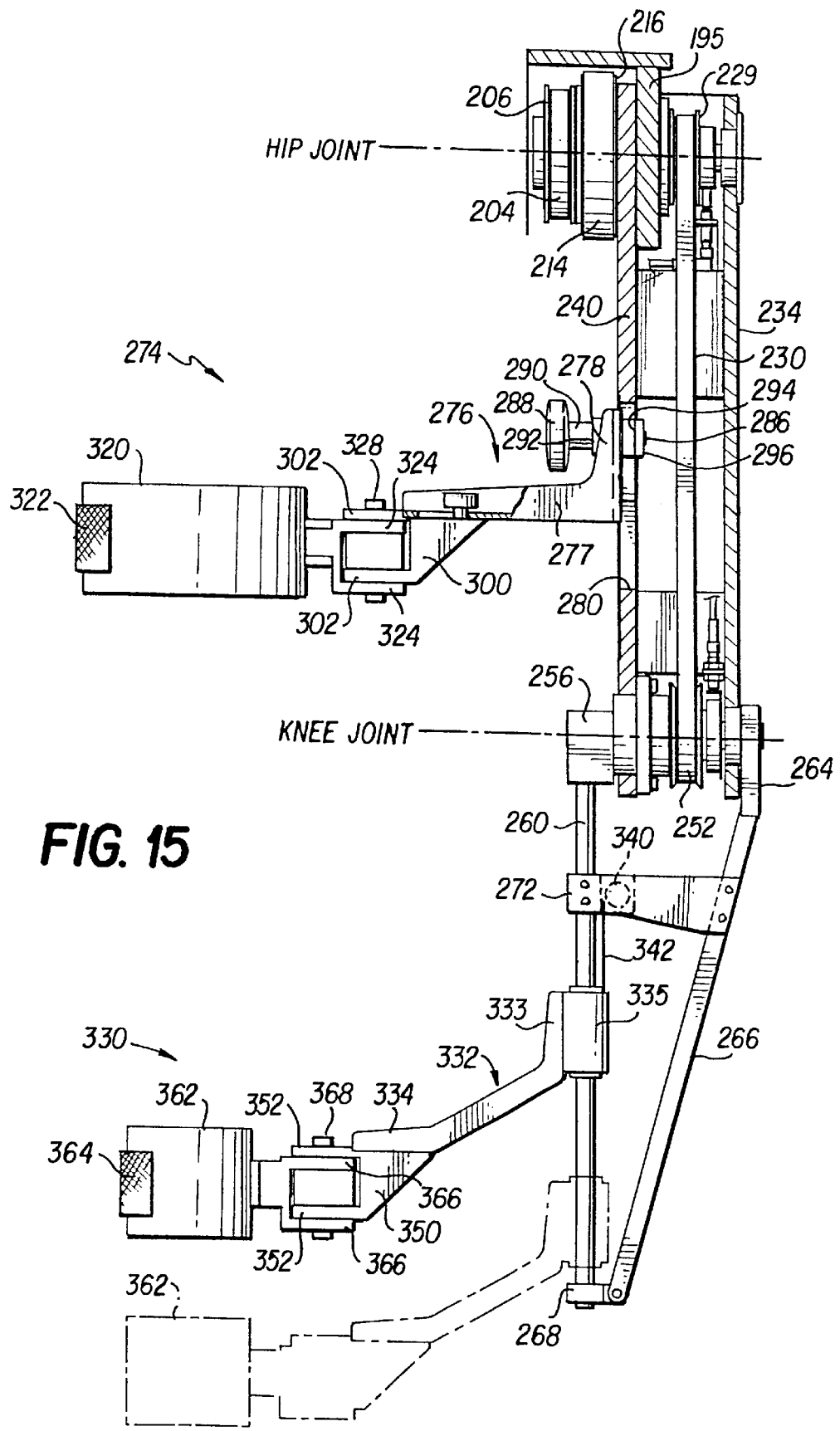
FIG. 15 is an enlarged end view, partly in section, of the support arm shown in FIG. 14.

As seen in FIGS. 13, 14 and 15, the post 160 and support arm 195 appearing at the top of FIG. 11 are illustrated. A servo motor 200 is connected to a gear box 201 which is connected as by bolting to support arm 195. An output pulley 202 is connected to the output of gear box 201. A belt 204 is trained over pulley 202 and a pulley 206 hereinafter described. A servo motor 210 is connected to gear box 211 which is connected as by bolting to support arm 195. An output pulley 212 is connected to the output of gear box 211. A belt 214 is trained over pulley 212 and a pulley 216 hereinafter described.

Figure 16:
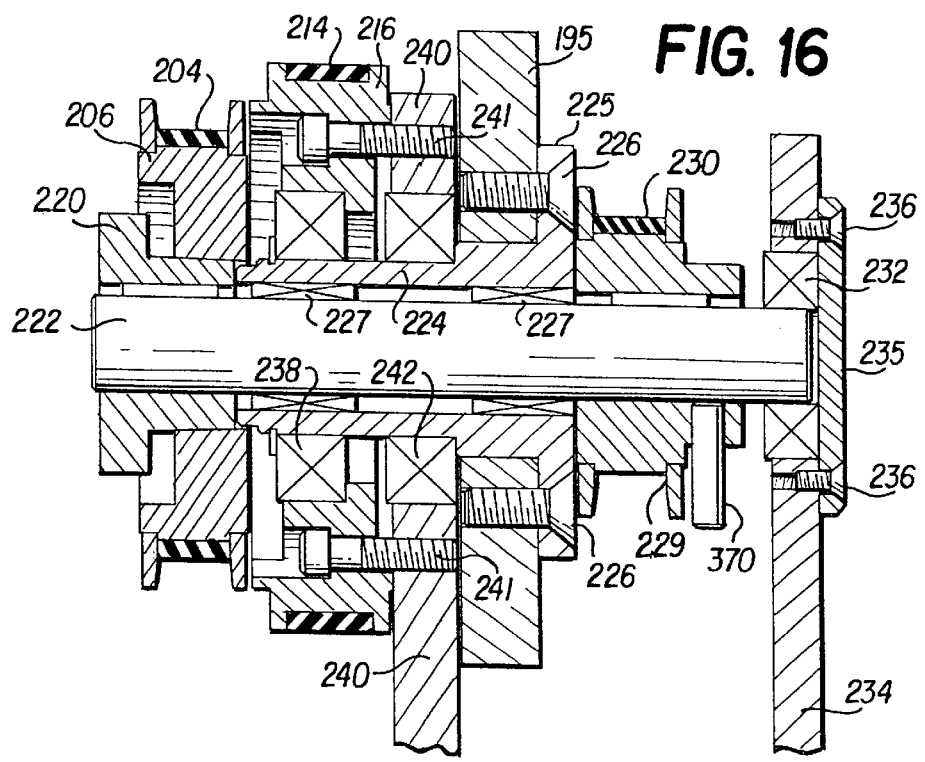
FIG. 16 is an enlarged section through the hip joint portion of the structure shown in FIG. 15.

Referring to FIG. 16, the hip joint of the device is shown in detail. Pulley 206 is of annular construction and has a member 220 secured thereto as by a tapered bushing arrangement including bolts (not shown), member 220 being keyed to a shaft 222 for rotation therewith. Arm 195 has a hole formed therein which receives a tubular member 224 having a flange 225 thereon which is bolted to the arm by bolts 226. Needle bearings 227 are disposed within tubular member 224 and rotatably support shaft 222. A pulley 229 is keyed to shaft 222 for rotation therewith. A belt 230 is trained over pulley 229 for a purpose hereinafter described.

Bearing 232 is supported on the right-hand end of shaft 222 and serves to rotatably support the upper end of a member 234 forming part of a first depending arm assembly hereinafter described. An end cap 235 is disposed over bearing 232 and is secured to member 234 by bolts 236. Pulley 216 is rotatably supported on bearing 238 which is supported on the outer surface of member 224. The pulley is secured to a member 240 by bolts 241, member 240 being rotatably supported on bearing 242 which is supported on the outer surface of member 224. Member 240 also forms part of the first depending arm assembly. As seen in FIG. 15, members 234 and 240 extend downwardly from the hip joint and form a first depending arm assembly which has a knee joint disposed at the lower end thereof.

Figure 17:
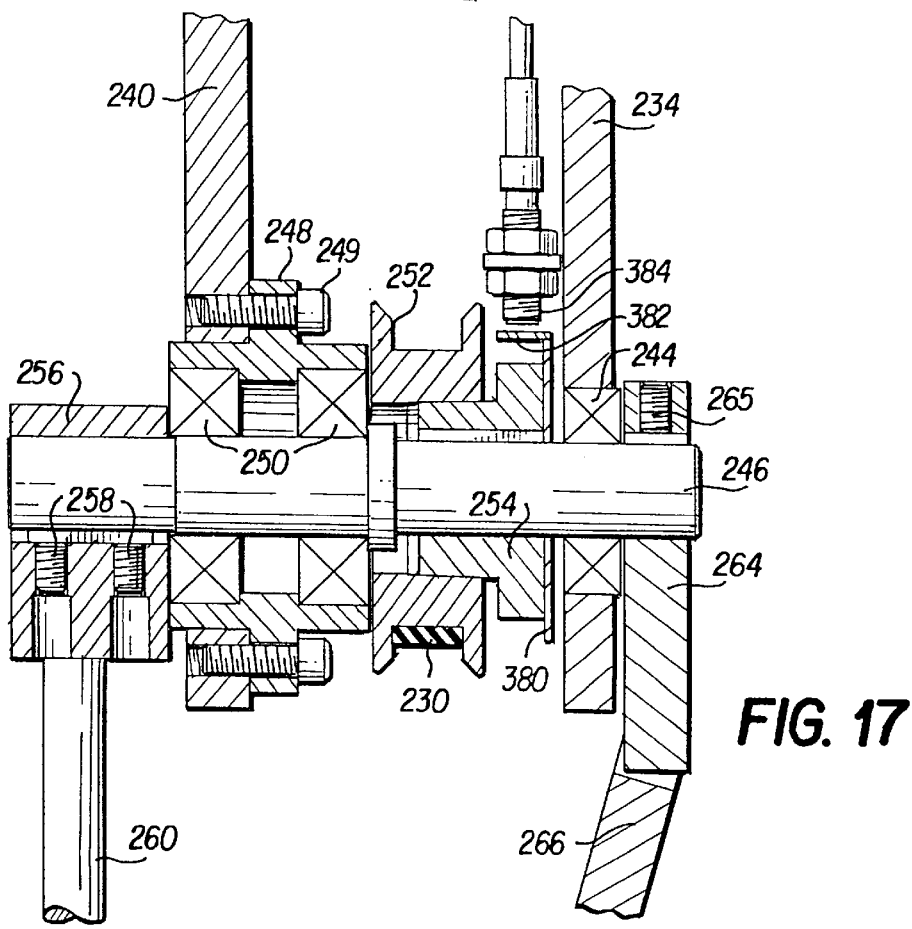
FIG. 17 is an enlarged section through the knee joint portion of the structure shown in FIG. 15.

Referring to FIG. 17, the knee joint of the device is shown in detail. A bearing 244 is supported at the lower end of member 234. A shaft 246 has one end thereof rotatably mounted within bearing 244. The lower end of member 240 has a hole formed therein within which a bearing retainer 248 is disposed, the bearing retainer being secured to member 240 by bolts 249. A pair of bearings 250 are disposed within retainer 248 and rotatably support shaft 246 at spaced points therealong. A pulley 252 has belt 230 trained therearound and the pulley is secured to member 254 by a tapered bushing arrangement including bolts (not shown), member 254 being keyed to shaft 246 for rotation therewith.

A fitting 256 has a bore receiving the left-hand end of shaft 246, and the fitting is fixed to the shaft for rotation therewith by a key and is held in place by set screws 258. Fitting 256 carries a pair of spaced downwardly extending rods 260, one of which is visible in FIG. 17, for a purpose hereinafter described. A brace mount 264 is fixed to shaft 246 for rotation therewith by a key and is held in place by a set screw 265. A brace member 266 is connected to the brace mount as by bolting and extends downwardly to a fitting 268 which is connected as by bolting to the lower ends of rods 260 and the brace member as seen in FIGS. 14 and 15. A support block 270 receives the rods 260 which pass through bores in the support block. A pair of plates 272 extend between block 270 and a brace member 266 and are connected thereto as by bolting.

As seen in FIGS. 14 and 15, a thigh cuff assembly 274 includes a support member 276 having a horizontal portion 277 and a vertical portion 278. A slot 280 is formed in depending member 240. As seen particularly in FIG. 14, the inwardly facing face of member 240 has a recess 282 formed therein which receives a reduced part of the vertical portion 278 therein so that the vertical portion is adapted to slide vertically within the recess but cannot turn relative to member 240. A through hole 284 is formed in vertical portion 278 for receiving a reduced threaded stem portion 286 of an adjusting knob 288 which is seen in FIG. 15, but has been removed as seen in FIG. 14. The knob includes a portion 290 which abuts a collar 292 formed on vertical portion 278. A nut 294 has a threaded hole formed therethrough which receives the threaded stem portion of the adjusting knob. Nut 294 has opposite flat sides which are slidably received within slot 280 so that the nut may move vertically within the slot but cannot turn relative thereto. Flanges 296 extend laterally from the opposite flat sides of the nut and engage the inner face of member 240 so that the nut cannot pass through slot 280. It is apparent that by loosening and tightening knob 288, the vertical position of member 276 can be manually adjusted.

A bracket 300 includes two lugs 302 extending therefrom. The bracket is connected to the horizontal portion of support member 276 for horizontal adjustment relative thereto. If a vertical section were taken through horizontal portion 277 looking toward the inwardly facing face of member 240, the horizontal portion has a generally H-shaped cross-section with the opposite legs of the H forming the sides of the horizontal portion 277 with the sides being connected by a horizontal web section 304. This web section has an elongated slot 306 formed therethrough extending in a direction perpendicular to the inwardly facing face of member 240. A threaded bolt 308 extends through the slot and is threaded into a threaded hole (not shown) formed in the upper surface of a bracket 300 which fits between the lower legs of the H-shaped cross-section of horizontal portion 277. The horizontal position of the bracket can be adjusted by loosening the bolt and moving the bracket horizontally, whereupon the bolt can be tightened to hold the bracket in adjusted position.

An arcuate thigh cuff 320 includes a strap 322 provided with VELCRO fastening portions for fastening the thigh cuff to the thigh of a patient just above his knee. The thigh cuff includes a pair of integral lugs 324 which abut lugs 302 on bracket 300, a pivot pin 328 extending through aligned holes in the lugs to pivotally support the thigh cuff on the bracket.

An ankle cuff assembly 330 includes a support member 332 having a vertical portion 333 and a horizontal portion 334. A pair of linear bearings 335 are slidably disposed on depending rods 260, the two bearings being connected to one another by a plate which is in turn secured to vertical portion 333 of support member 332 as by bolting. A constant force counter balance spring 340 is supported between plates adjacent support block 270 and is shown in dotted lines in FIG. 15. This spring is conventional and includes a band 342 interconnected to the vertical portion of support member 332 for counterbalancing the weight of the ankle cuff assembly.

A bracket 350 includes two lugs 352 extending therefrom. The bracket is connected to the horizontal portion of support member 332 for horizontal adjustment relative thereto. This horizontal adjustment is identical to and operates in the same manner as the horizontal adjustment connection between support member 276 and bracket 300 previously described.

An arcuate ankle cuff 362 includes a strap 364 provided with VELCRO fastening portions for fastening the ankle cuff to the ankle of a patient. The ankle cuff includes a pair of integral lugs 366 which abut lugs 352 on bracket 350, a pivot pin 368 extending through aligned holes in the lugs to pivotally support the ankle cuff on the support member 332. The ankle cuff assembly 330 is also shown in phantom line in FIG. 15 to illustrate the manner in which the assembly may float vertically along rods 260 to adjust the ankle cuff in accordance with the height of the patient.

Referring to FIGS. 18, and 18a as well as FIG. 16, a metallic indexing pin 370 is fixed to pulley 229. A metal sensor 372 is mounted on bracket 374 which is secured by bolts 375 to cross member 376 which has the opposite ends thereof secured as by bolting to the inner facing surfaces of members 240 and 234. This sensor is connected with the control means to sense the knee joint home position.

Referring to FIGS. 18, 18b as well as FIG. 17, a metal target 380 having an outer arcuate flange portion 382 is secured to pulley 252 as by bolting. A pair of metal sensors 384 and 386 are mounted on bracket 388 which is secured as by bolting to cross member 390 which has the opposite ends thereof secured as by bolting to the inner facing surfaces of members 240 and 234. These sensors cooperate with flange 382 to sense whether or not the flange has moved beyond either sensor and are connected with the control means to sense over-travel of the knee joint in opposite directions.

Figure 19:
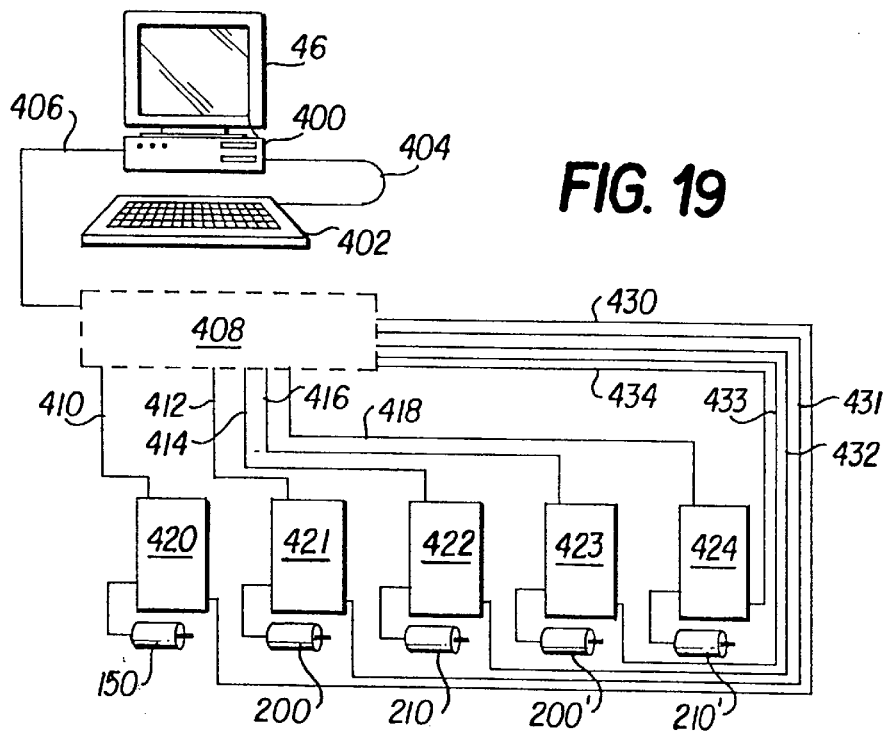
FIG. 19 is a schematic wiring diagram of the control system.

Referring to FIG. 19, the control means of the invention is schematically illustrated wherein the touch screen 46 is electrically connected to a computer or programmable logic controller (PLC) 400 having a suitable program incorporated therein. A conventional keyboard 402 is electrically connected to the computer by a lead 404. A lead 406 connects the computer to a motion controller 408 which in actual practice is a servo motion card disposed inside the computer. The motion controller is connected by leads 410, 412, 414, 416 and 418 with servo drives 420, 421, 422, 423 and 424 respectively. The servo drives are connected to the servo motor 150 for the treadmill, servo motor 200 for the right knee drive and 210 for the right hip drive. Servo motors 200' and 210' correspond to the servo motors 200 and 210 respectively, but are supported by the leg actuator assembly on the opposite side of the treadmill to provide the left knee drive and the left hip drive. Leads 430, 431, 432, 433 and 434 provide feedback from the servo drives to the motion controller and thence to the computer program. The hip and knee joint servos are slaved to the treadmill servos so that the various drive means operate in a coordinated manner to cause the legs of a patient to move in a desired gait. The control panel 42 is connected to the servo motors controlled thereby by suitable electrical cables 440 as seen in FIGS. 1 and 1a.

Figure 20:
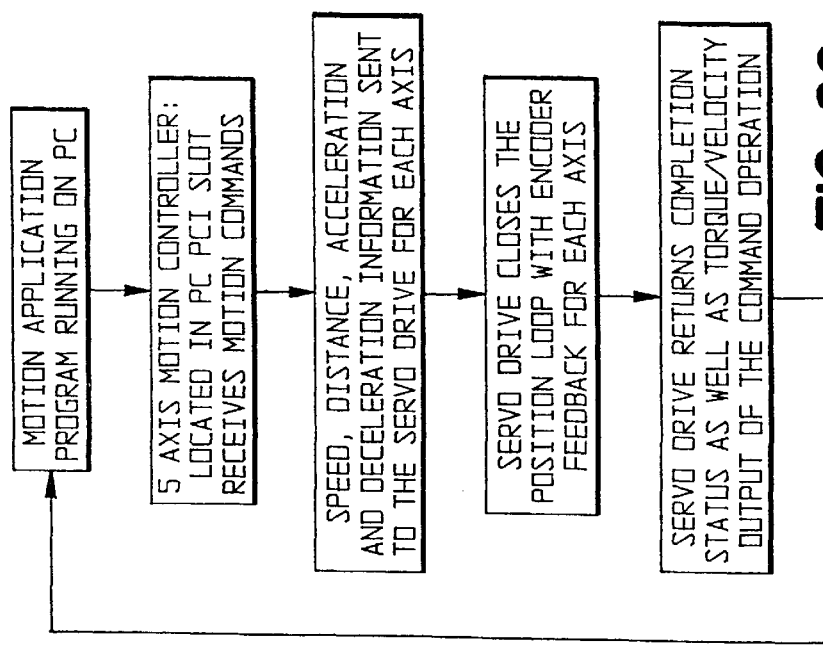
FIG. 20 is a flow chart of the functions performed by the control means.

Referring now to FIG. 20, a flow chart sets forth the various functions performed by the schematic control means illustrated and described above in connection with FIG. 19. The flow chart is self-explanatory and is readily understood by one skilled in the art.

The invention has been described with reference to a preferred embodiment. Obviously, various modifications, alternatives and other embodiments will occur to others upon reading and understanding this specification. It is my intention to include all such modifications, alternatives and other embodiments insofar as they come within the scope of the appended claims or equivalents thereof.

What is claimed is:

1. A powered gait orthosis comprising, a support structure, lifting means supported on said support structure for connection to a lifting harness secured to a patient, a treadmill for acting on the feet of a patient, said treadmill including opposite sides and opposite ends, drive means for driving said treadmill, a pair of spaced leg actuator assemblies disposed adjacent to said opposite sides of the treadmill, said leg actuator assemblies each including a support arm, a first depending arm supported by said support arm for pivotal movement about a first generally horizontal axis, a second depending arm supported by said first depending arm for pivotal movement about a second generally horizontal axis, depending arm drive means for moving said first and second depending arms about the pivot axes thereof, first attachment means for attaching said first depending arm to a patient's leg just above the knee of the patient's leg, second attachment means for attaching said second depending arm to a patient's leg at the ankle of the patient's leg, and control means connected to the drive means for said treadmill and the drive means for said first and second depending arms to direct the various drive means to operate in a coordinated manner to cause the legs of a patient to move in a desired gait.

2. A device as defined in claim 1 wherein at least one of said support arms is substantially horizontal and is mounted for swinging movement about a vertical axis so as to swing outwardly away from said treadmill.

3. A device as defined in claim 2 including locking means for locking said support arm in operative position.

4. A device as defined in claim 1 wherein said lifting means is movably mounted on said support structure.

5. A device as defined in claim 4 wherein said lifting means includes a parallelogram linkage.

6. A device as defined in claim 1 wherein said treadmill is interconnected to said leg actuator assemblies.

7. A device as defined in claim 1 wherein the drive means for moving said first and second depending arms of each leg actuator assembly comprises a pair of servo motors supported by the support arm of the associated leg actuator assembly.

8. A device as defined in claim 7 wherein a first one of said servo motors is interconnected by a first belt and a second belt with a first pulley drivingly connected to said second depending arm, and a second one of said servo motors is interconnected by a third belt with a second pulley drivingly connected to said first depending arm.

9. A device as defined in claim 8 wherein said first belt is interconnected with a third pulley which is drivingly connected to said first pulley by a third belt.

10. A device as defined in claim 1 wherein said first attachment means is supported on said first depending arm and is vertically adjustable relative thereto.

11. A device as defined in claim 10 wherein said first attachment means includes a support member, and including locking means for locking said support member in adjusted position relative to said first depending arm.

12. A device as defined in claim 11 wherein said first attachment means includes a first attachment cuff pivotally supported by said support member.

13. A device as defined in claim 12 wherein said first attachment cuff is horizontally adjustable relative to said support member, and including locking means for locking said first attachment cuff in adjusted position relative to said support member.

14. A device as defined in claim 1 wherein said second attachment means is supported by said second depending arm said second depending arm including a guide rod, said second attachment means including a linear bearing slidably mounted on said guide rod, and a constant force counter balance spring being connected to said linear bearing.

15. A device as defined in claim 14 including a laterally extending arm connected to said linear bearing, said second attachment means including a second attachment cuff pivotally supported by said arm.

16. A device as defined in claim 15 wherein said second attachment cuff is horizontally adjustable relative to said arm, and including locking means for locking said second attachment cuff in adjusted position relative to said arm.

17. A device as defined in claim 1 wherein said second axis defines a knee joint axis, and including a first and second sensor means supported by said first depending arm, said first sensor means sensing the knee joint home position, and said second sensor means sensing over-travel of the knee joint.

18. A device as defined in claim 1 including a control panel supported by said support structure adjacent one end of said treadmill, a pivoted linkage extending from said panel and supporting a touch screen data entry/display device.

19. A powered gait orthosis comprising, a rigid framework, lifting means mounted on said framework and adapted to be secured to a lifting harness attached to a patient, a treadmill for acting on the feet of a patient, said treadmill having opposite sides, drive means for said treadmill, a pair of spaced leg actuator assemblies disposed at said opposite sides of the treadmill, said leg actuator assemblies each including a housing, a support arm supported by said housing, adjusting means for moving said support arm vertically with respect to said housing, a first depending arm having upper and lower ends, the upper end of said first depending arm being pivotally supported by said support arm, a second depending arm having upper and lower ends, the upper end of said second depending arm being pivotally supported by the lower end of said first depending arm, first depending arm drive means for moving said first depending arm about the pivot axis thereof, second depending arm drive means for moving said second depending arm about the pivot axis thereof, first attachment means adjacent the lower end of said first depending arm for attaching said first depending arm to a patient's leg just above the knee of the patent's leg, second attachment means adjacent the lower end of said second depending arm for attaching said second depending arm to a patient's leg at the ankle of the patient's leg, and control means connected to the drive means for said treadmill and the drive means for said first and second depending arms to direct the various drive means to operate in a coordinated manner to cause the legs of a patient to move in a desired gait.

20. A device as defined in claim 19 wherein said lifting means is movably mounted on said framework.

21. A device as defined in claim 20 including rails mounted on said framework, said lifting means being slidable along said rails.

22. A device as defined in claim 21 including locking means for locking said lifting means in operative position along said rails.

23. A device as defined in claim 19 wherein said adjusting means comprises a carriage movable along guide rods supported by said housing, said carriage being connected to said support arm.

24. A device as defined in claim 23 including drive means connected with a lead screw engaging a threaded bushing carried by the carriage for moving the carriage in opposite vertical directions.

25. A device as defined in claim 19 including a pair of hand holds extending toward one another, each of said hand holds being supported by one of said housings.

26. A device as defined in claim 19 wherein said support arm is substantially horizontal and is mounted for swinging movement about a generally vertical axis so as to swing outwardly away from said treadmill.

27. A device as defined in claim 19 wherein said treadmill is connected to each of said housings.

28. A device as defined in claim 19 wherein said first attachment means is supported by said first depending arm and includes a first attachment cuff the position of which is adjustable both horizontally and vertically with respect to said first depending arm.

29. A device as defined in claim 19 wherein said second attachment means is supported by said second depending arm and includes a second attachment cuff the position of which is adjustable both horizontally and vertically with respect to said second depending arm.

30. A device as defined in claim 29 wherein said second attachment cuff floats vertically by being slidably mounted on a guide rod of said second depending arm.

* * * * *